United States Patent [19]

Strahle

[11] Patent Number: Plant 5,381

[45] Date of Patent: Jan. 1, 1985

[54] ROSE PLANT 'LITTLE CAMEO'

[75] Inventor: Robert Strahle, Carlton, Oreg.

[73] Assignee: Carlton Rose Nurseries, Inc., Carlton, Oreg.

[21] Appl. No.: 452,090

[22] Filed: Dec. 22, 1982

[51] Int. Cl.[3] ..... A01H 5/00

[52] U.S. Cl. ..... Plt./18

[58] Field of Search ..... Plt./18, 22

*Primary Examiner*—James R. Feyrer

*Attorney, Agent, or Firm*—Chernoff, Vilhauer, McClung, Birdwell & Stenzel

[57] ABSTRACT

A rose plant of the grandiflora class obtained as a seedling from a seed parent LARA and an unnamed pollen parent provides an abundance of long-lasting blooms having a spicy fragrance which maintain their true color from bud through leaf drop, on a continuous basis in a greenhouse.

14 Drawing Figures

BACKGROUND AND SUMMARY OF THE INVENTION

The present invention relates to a new and distinct variety of Grandiflora rose plant, a seedling resulting from a definite effort to produce an improvement in this class of rose and marketed under the variety name "Little Cameo".

The primary feature of this new variety which connotes its distinctive advantage over existing types are its ability to abundantly yield a quantity of cut flowers under greenhouse conditions which maintain true color after being cut, from bud through petal drop.

The variety of rose of the present invention was obtained at Hillsboro, Oreg. as a seedling from a seed parent of the LARA variety (U.S. Plant Pat. No. 2,986), and an unnamed pollen parent. The crossing was made in April, 1978, the sowing in November of 1978, and the first flower appeared in February of 1979.

Asexual reproduction of my new and distinct variety shows that its unique combination of characteristics come true to form and are established and transmitted through succeeding generations by budding.

BRIEF DESCRIPTION OF THE DRAWINGS

The accompanying photographs show typical specimens of the vegetative growth and flowers of the new variety in different stages of development and are depicted in color as nearly true as is reasonably possible to make the same in color illustrations of this character.

FIG. 1 shows a developing flower bud;

FIG. 2 shows a flower bud as the sepals start to crack;

FIG. 3 shows a nearly open flower bud in the cutting stage;

FIG. 4 shows an open flower;

FIG. 5 shows flower petals with the inside of the petal above and the outside of the petal below;

FIG. 6 shows the flower with the petals removed exposing the anthers and stamens;

FIG. 7 shows a flower with the petals, stamens, and anthers removed exposing the pistils;

FIG. 8 shows a flower with the petals removed cut in cross-section exposing the receptacle, stamens, and pistils;

FIG. 9 shows a section of the flower stem at the point of branching;

FIG. 10 shows the upper side of a compound leaf;

FIG. 11 shows the lower side of a compound leaf with petiole and rachis;

FIG. 12 shows a ripe rose hip;

FIG. 13 shows a flowering stem with leaves and flower removed;

FIG. 14 shows a composite of several flowers in different stage of development from tight bud to open flower.

DETAILED DESCRIPTION OF THE DISCLOSURE

The following description was made during January, 1982 of the rose plant of the new and distinct variety growing in a greenhouse in Carlton, Oreg. Color designations are to *Dictionary of Color*, by Maerz and Paul.

FLOWER

Flowers borne: Singly on normal strength, medium length stems.

Quantity of bloom: Abundant in greenhouse.

Continuity: Continuous.

Fragrance: Moderate; spicy.

Bud:

*Peduncle.*—Medium length; medium weight; erect; medium green; almost smooth; few, red, prickles.

*Before calyx breaks.*—Size: medium. Form: pointed with a conspicuous neck; without foliaceous appendages on the surface of the bud.

*As calyx breaks.*—Color: 2-A-5.

*As first petal opens.*—Size: medium. Form: Medium length; flat. Color: Outside: 49-H-1. Inside: 50-K-2. Opening: It does open up well.

Bloom: Size when fully open: medium; 2½ inches to 3 inches.

*Petalage.*—Double; from 22 to 25 petals; arranged regularly.

*Form.*—High centered at first; becoming open centered; petals remaining at first tightly capped inward; becoming later at maturity loosely rolled outward.

Petals: Medium thick; satiny inside and outside.

*Shape.*—Outer: Obovate; with one notch. Intermediate: Obovate; with one tooth. Inner. Obovate; with one notch.

*Color.*—Colors may be modified by being shaded with other colors.

Color of newly opened flower:

*Outer petal.*—Outside surface: 49-H-1. Inside surface: 50-K-2.

*Intermediate petal.*—Outside surface: 49-H-1. Inside surface: 50-K-2.

*Inner petal.*—Outside surface: 49-H-1. Inside surface: 50-K-2.

Color of flowers three days after opening:

*Outer petal.*—Outside surface: 50-K-2.

*Inner petal.*—Outside surface: 49-H-1. Inside surface: 50-K-2.

General color effect:

*Newly opened flower.*—Light pink with darker shading on outer edges of petals giving a pink-blend effect.

*Flowers three days open.*—Outer edges darker than body of petals giving a translucent effect.

Behavior: Persist.

Flower longevity: Cut roses grown in greenhouse kept at living room temperature eight days during January.

REPRODUCTIVE ORGANS

Stamens: medium number; arranged regularly about pistils.

Filaments: Many; with anthers; short.

Color: 9-B-1.

Anthers: Open at various times; small.

*Color.*—9-L-10. Seldom fused with a petaloid.

Pollen: Very sparse; 9-J-10.

Pistils: Medium number.

Styles: Even; medium length; medium thickness; bunched.

Stigma: 9-J-2.

Ovaries: Some protruding from receptacle.

Hips: Medium-long with inconspicuous neck; very smooth; thick walls; green-yellow when first formed, changing to 1-E-12 when ripe.

Sepals: Permanent; moderately long; spear-shaped, curled.

Seeds: Medium number; small.

PLANT

Foliage:

*Leaves.*—Compound of 3 and 5 leaflets; moderately abundant; medium sized; moderately leathery; wrinkled.

*Leaflets.*—Shape: oval, apex acute, base round, margin simply serrate.

Color: Mature upper surface: 24-H-2. Mature under surface: 23-E-6. Young upper surface: 24-J-11. Young under surface: 5-I-3.

*Rachis.*—Medium. Upper side: smooth grooved. Under side: smooth.

*Stipules.*—Medium length; medium width; very short points; turning out at an angle of less than 90°.

*Disease.*—Resistance comparable to the average variety growing under the same cultural conditions.

GROWTH

Habit: Upright; much branched.

Growth: Very vigorous.

Canes: Medium.

Main stems: Bright.

*Color.*—22-D-11.

*Prickles.*—Few. Color: 7-L-7.

*Hairs.*—None.

Branches: bright.

*Color.*—24-L-3.

*Prickles.*—Few. Color: 15-L-11.

*Hairs.*—None.

New shoots: bright.

*Color.*—5-K-6.

*Prickles.*—Several. Color: 4-H-5.

*Hairs.*—None.

I claim:

1. A new and distinct variety of rose plant of the grandiflora-class, substantially as described and illustrated, obtained as a seedling from a seed parent LARA and an unnamed pollen parent, characterized by its ability to abundantly yield, long-lasting blooms having a spicy fragrance on a continuous basis in a greenhouse which maintain true color from a bud through petal drop, substantially as shown.

* * * * *

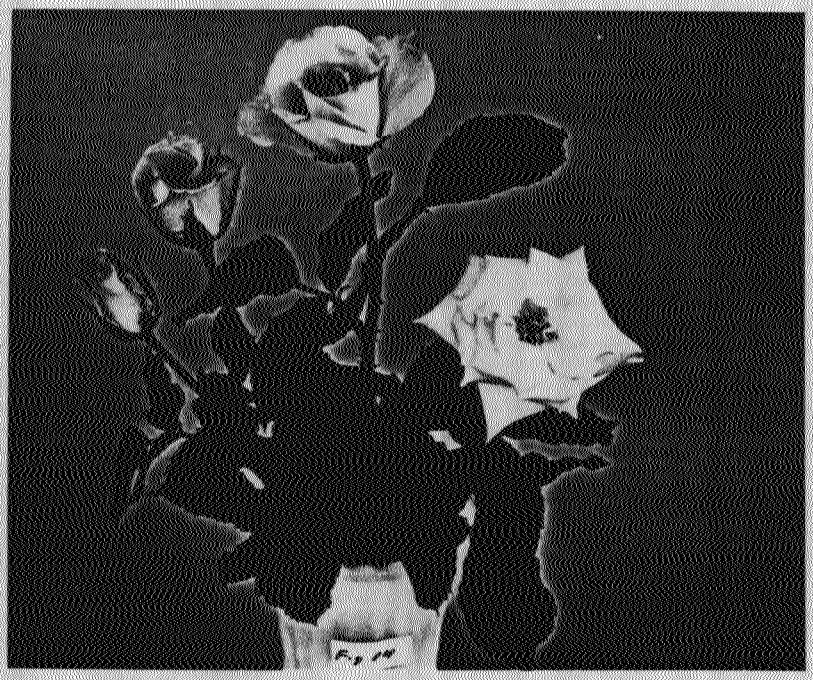
Fig. 14
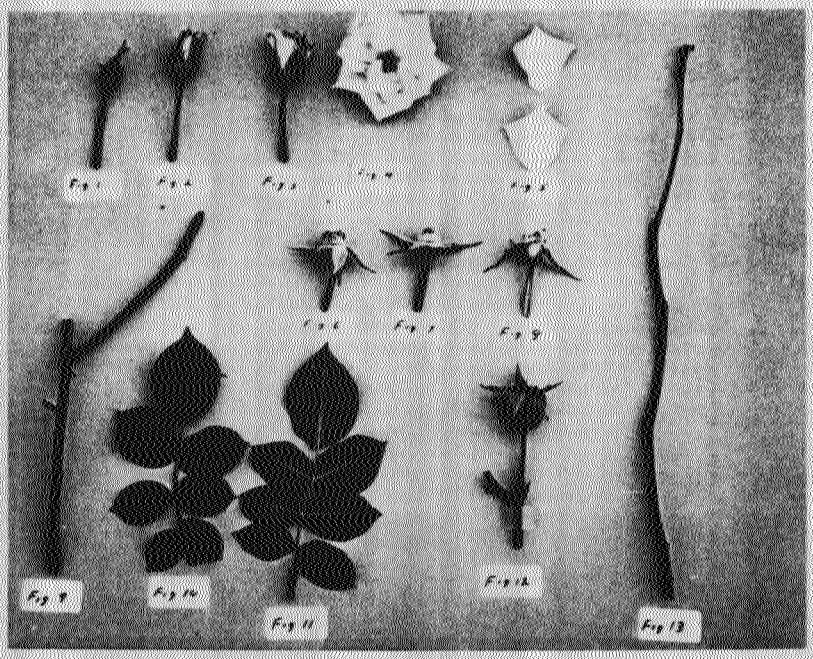

UNITED STATES PATENT AND TRADEMARK OFFICE

CERTIFICATE OF CORRECTION

PATENT NO. : Plant Patent No. 5381

DATED : January 1, 1985

INVENTOR(S) : Robert Strahle

It is certified that error appears in the above-identified patent and that said Letters Patent is hereby corrected as shown below:

Col. 3, line 8 change "50-K-2" to --49-H-1 --

Col. 4, line 6 change "24-H-2" to -- 24-H-8 --

Signed and Sealed this

*Third* Day of *September 1985*

[SEAL]

*Attest:*

DONALD J. QUIGG

*Attesting Officer* *Acting Commissioner of Patents and Trademarks - Designate*